United States Patent [19]

Goldhardt et al.

[11] Patent Number: 5,336,203
[45] Date of Patent: Aug. 9, 1994

[54] LOW PROFILE GASTROSTOMY DEVICE WITH DOME

[75] Inventors: Donald J. Goldhardt, Grove City; William H. Hirsch, Columbus, both of Ohio

[73] Assignee: Abbott Laboratories, Abbott Park, Ill.

[21] Appl. No.: 69,038

[22] Filed: May 28, 1993

[51] Int. Cl.$^5$ .............................................. A61M 5/00
[52] U.S. Cl. ........................... 604.7/247; 604/256; 604/27; 604/332; 604/335
[58] Field of Search ............ 604/27, 28, 30, 34, 604/96, 170, 244, 247, 256, 332, 335, 337, 174

[56] References Cited

U.S. PATENT DOCUMENTS

| | | |
|---|---|---|
| 2,230,226 | 2/1941 | Auzin . |
| 2,487,630 | 11/1949 | Alvarez ................................. 604/96 |
| 2,649,092 | 8/1953 | Wallace . |
| 2,687,131 | 8/1954 | Raiche . |
| 3,154,077 | 10/1964 | Cannon . |
| 3,253,594 | 5/1966 | Matthews et al. . |
| 3,812,841 | 5/1974 | Isaacson . |
| 3,915,171 | 10/1975 | Shermeta . |
| 3,961,632 | 6/1976 | Moosun . |
| 3,982,544 | 8/1976 | Dyck . |
| 4,083,369 | 4/1978 | Sinnreich ................................. 604/96 |
| 4,315,513 | 2/1982 | Nawash et al. . |
| 4,393,873 | 7/1983 | Nawash et al. . |
| 4,416,273 | 11/1983 | Grimes . |
| 4,666,433 | 5/1987 | Parks . |
| 4,863,438 | 9/1989 | Gauderer et al. . |
| 4,944,732 | 7/1990 | Russo . |
| 5,125,897 | 6/1992 | Quinn et al. ........................... 604/247 |
| 5,169,393 | 12/1992 | Moorehead etal. . |
| 5,201,722 | 4/1993 | Moorehead et al. . |
| 5,261,459 | 11/1993 | Atkinson et al. . |
| 5,269,763 | 12/1993 | Boehmer et al. .................... 604/256 |

OTHER PUBLICATIONS

Gauderer et al, "Feeding Gastrostomy Button: Experience and Recommendations", Journal of Pediatric Surgery, vol. 23, No. 1, pp. 24-28 (1988).
Goldhardt et al, Appln. Ser. No. 8/069,035, filed May 28, 1993, for "Low Profile Gastrostomy Device With One-Way Cross-Slit Valve".

*Primary Examiner*—C. Fred Rosenbaum
*Assistant Examiner*—N. Kent Gring
*Attorney, Agent, or Firm*—Lonnie R. Drayer; Donald O. Nickey

[57] ABSTRACT

A gastrostomy device for easier insertion into an established stoma is provided with an apertured dome connected at its bottom wall to a tubular shaft, wherein the dome is particularly characterized by having the sidewall thinned from apex to bottom wall whereby the dome, when elongated with an obturator, stretches smoothly and readily to very close to the diameter of the tubular shaft. The device is ordinarily provided with a one-way valve mounted in the dome as well as with a retention flange at the outer end of the tubular shaft. Preferably the one-way valve is a cross-slit duckbill valve of novel design.

23 Claims, 11 Drawing Sheets

LOW PROFILE GASTROSTOMY DEVICE WITH DOME

FIELD OF THE INVENTION

The invention relates to a gastrostomy device for easier insertion into a stoma in replacement of a gastrostomy device that has been removed intentionally or accidently.

DESCRIPTION OF RELATED ART

Gastrostomies now assume a key role in the management of patients with swallowing difficulties due to injury or disease, as well as those patients requiring long term enteral feedings. In the most widely used gastrostomies of the recent past, access to the stomach has been had by a catheter, usually of the de Pezzer or Foley type. Although simple to use, these catheters have several disadvantages and are associated with a variety of complications, such as, internal or external migration, inadvertent removal, pivoting action leading to leakage and tissue reaction.

To overcome these problems rather simple skin-level silicone rubber devices have been developed which are designed to be inserted from the external or skin side into a stoma of an established gastrostomy. Each of these devices has a shaft in the form of a short tube or conduit extending from an inner bulb or dome, often of mushroom-like shape resembling the tip of a de Pezzer catheter, and with one or more perforations for liquid passage, to an external or outer portion that is self retaining, e.g., with flat wings or a ridged or perforated flat flange. A valve, usually at the gastric opening of the shaft, prevents external reflux of intragastric contents. A small cap or plug at the skin level is removed and a simple hollow adapter is inserted into the shaft for feeding. The valve may have low opening pressure or the adapter may be inserted through the valve. Feeding accomplished, the tube or shaft is flushed with water, the adapter removed, and the cap or plug replaced.

U.S. Pat. No. 4,315,513 describes a gastrostomy or transport tube of the type referred to above, in this case with a check valve within the shaft with a valve stem attached to a hemispherical element that seats into a mating cavity when there is pressure within the stomach, with the valve stem extending through the bottom of the seat as a guide. In an alternative form of this device there is used a hemispherical bulb or dome of a soft rubber that is diametrically slit so that no internal check valve is needed. The wall of the bulb or dome is of uniform thickness similar to that of the shaft employed.

In U.S. Pat. No. 4,863,438 there is described a low profile gastrostomy device of the type referred to above with a hollow bulb-like internal retaining element with apertures for passage of fluids and with a flat flapper valve serving as a check valve. The flapper valve extends across the end of the shaft within the bulb-like retaining element. The bulb-like portion is of uniform wall thickness, the bottom portion being integrally formed with the shaft and the top portion being adhesively bonded to the bottom portion. The shaft at its outer or skin end is closed by a plug that is attached by a flexible membrane to the edge of one of the pair of flat wings or a flange that serves as the external retaining element.

In U.S. Pat. No. 4,944,732 there is described a device of the type referred to above that utilizes a hollow conical bulb or dome with at least one opening therethrough for passage of fluids and is of uniform wall thickness throughout. At the skin or feeding end, this device is provided with an externally threaded plug for closure, and, within the plug, a duckbill one-way slit valve that is removable during obturation or for decompression or for replacement thereof.

Each of the devices provided heretofore, while offering advances in the field, has suffered from certain drawbacks or problems, however. A significant problem arises from the trauma associated with insertion of the bulb or dome through the stoma and into the stomach. The emplaced dome must be large enough to have retaining action against withdrawal, yet it must elastically deform, stretching sufficiently when elongated by thrusting an obturator through the shaft and into it, to narrow it enough for passage through the stoma. In each of the devices used heretofore, sofar as it is known, the dome wrinkles, when elongated with an obturator, and while it becomes smaller in diameter, it does not approach the shaft diameter sufficiently so that passage through a stoma is not as easy as would be liked and causes trauma which it is very desirable to avoid.

Various types of valves have been used to prevent reflux of intragastric contents and these have been found to be frequently inefficient, or short lived, or inconvenient to handle when decompression is necessary. In some applications where a long shaft is used, a valve may not be required or desired.

SUMMARY OF THE INVENTION

It has now been discovered that a gastrostomy device that is easy to insert into an established stoma is provided on making the device with a hollow tubular shaft communicatingly connected at its inner end with the bottom wall of an apertured dome at about the center of the bottom wall, the dome having an apex and a defining sidewall that is circular in section, wherein the dome design is particularly characterized by the sidewall being thinned progressively and gradually as the diameter of the dome increases from about mid-height, and preferably from about two-thirds height, of the dome to the bottom wall, so that the dome, when elongated by the use of an obturator, elongates by stretching smoothly and evenly with substantially no wrinkling or puckering and readily narrows down substantially to the diameter of the tubular shaft. The resulting device of this construction and made of a medically acceptable elastomeric material exhibits a substantially smooth, even peripheral surface for the insertion of the dome and shaft into the established stoma of a patient with substantially no trauma because of the insertion. Preferably the sidewall of the dome decreases in thickness across the specified zone of increasing diameter of the dome by at least about 20%, more preferably by about 33%, but not exceeding about 50%.

Most preferably, to help assure avoidance of wrinkling of the dome during elongation and insertion through the stoma of a patient, the apertures through the wall of the dome are three in number and oval, the major axis of each aperture lying about on a shortest line from the apex to the bottom wall of the dome and an end of each oval aperture being adjacent the bottom wall.

For some uses as a feeding tube, the gastrostomy device of the invention does not require a one-way valve and may have an adjustable retention disc or flange on a shaft that is up to about one foot in length or longer to attach, e.g., to a reservoir of a fluid to be administered directly into the stomach.

But for most uses, the present device is preferably a low profile device with a short tubular shaft having the apertured dome of novel design mounted on the inner end of the shaft, the shaft being provided with a one-way valve affixed at either end, usually the inner end, to allow delivery of fluids into the stomach and yet to sealingly intercept and control the passageway of the shaft to prevent refluxing of intragastric fluids. The present device also has usually a retention flange or disc surounding the outer end of the short shaft and a plug or cap that is used to close the shaft between feedings or as needed.

The one-way valve may be a flapper valve, but preferably is a cross-slit duckbill valve with a foreshortened hollow cylindrical body axially aligned with the passageway and joined to the shaft. The passageway through the cylindrical body is entirely controlled by a transversely extending continuous ridge and valley web or wall with intersecting slits in an intersection of the ridges. Within the cylindrical body the ridge and valley web consists of two intersecting partially folded wall portions, the folds each being along a line constituting a ridge or apex, each folded wall being V-shaped in section, and each folded wall portion extending substantially diametrically of the cylindrical body and normal to each other with the V's both opening in the same axial direction of the cylindrical body, and, with the lines formed by the apex of each folded wall portion meeting at about right angles to form four quadrants, each wall portion ending midway around a quadrant where it meets and merges with and is integrally joined to the mutually intersecting wall portion to form a valley extending radially outwardly from the intersection of the apices as well as toward the direction of the end of the cylindrical body, the so-shaped integral wall being a continuous wall of substantially uniform thickness formed within the confines of the cylindrical body and integrally formed therewith, the apices lying in a common plane substantially diametric to the valve body and both being slit at the intersection of the two apices, forming intersecting slits extending entirely through the wall at the fold or land forming each apex, the apices facing toward the apex of the dome portion of the gastrostomy device.

Typically the slits are about 1.5 to about 2.5 millimeters long. Preferably the apices are flattened in the form of lands and the slits are formed or cut through the lands longitudinally thereof.

BRIEF DESCRIPTION OF THE PREFERRED EMBODIMENTS

Figure 11:
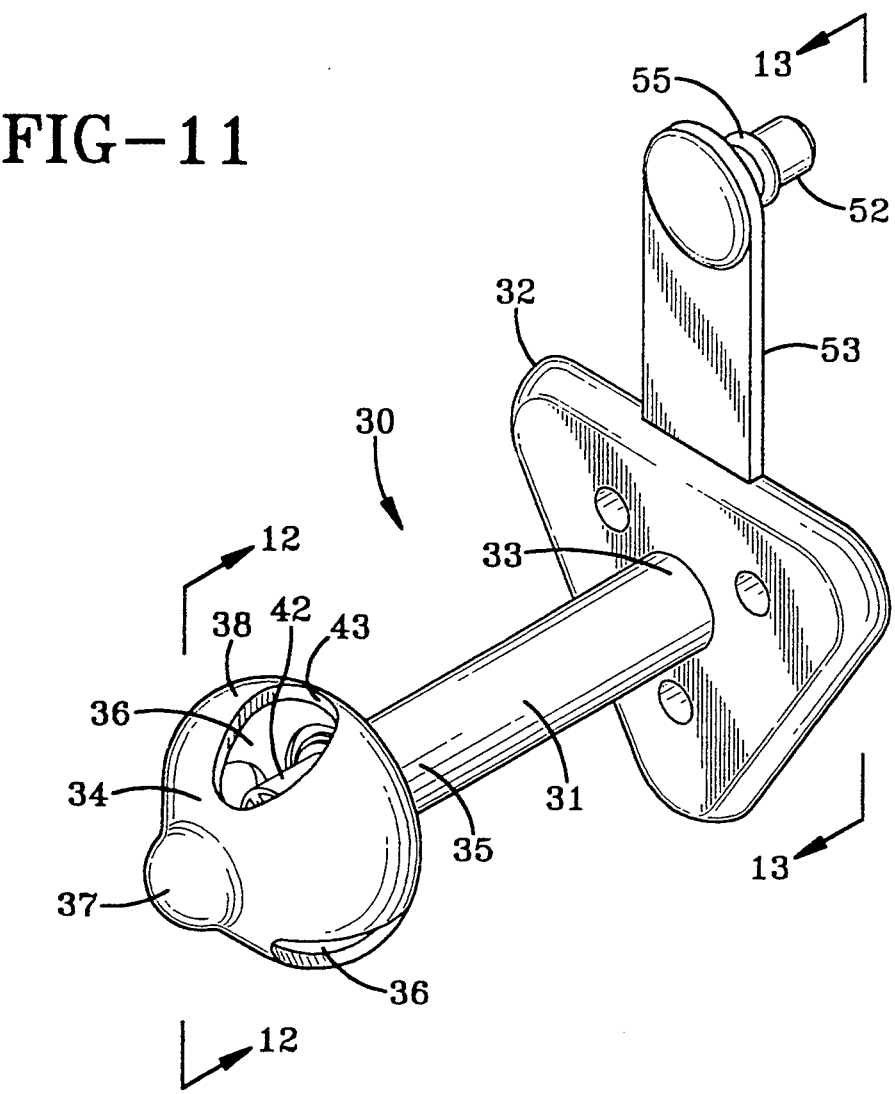
FIG. 11 is an isometric view of the low profile gastrostomy tube of the invention with a hollow shaft with a retaining element and attached plug at one end and the apertured dome of novel design at the other.
Figure 12:
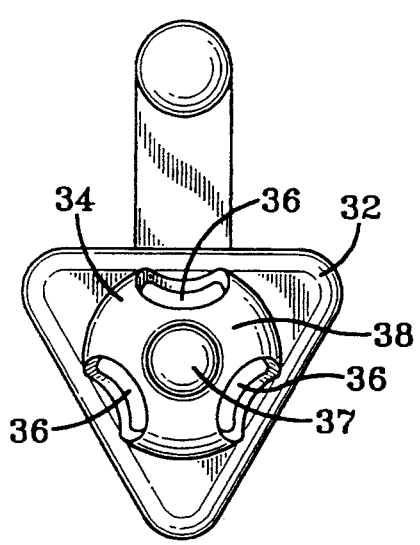
FIG. 12 is a view in front elevation of the novel gastrostomy tube taken along the lines 12—12 of FIG. 11.
Figure 13:
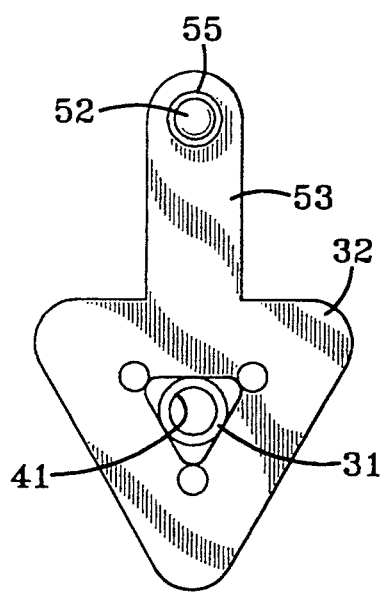
FIG. 13 is a view in rear elevation of the novel gastrostomy tube taken along the lines 13—13 of FIG. 11.

Referring now to FIGS. 11, 12 and 13, the novel low profile gastrostomy tube of the invention, indicated generally by the reference numeral 30, is seen to comprise a shaft, or connector tube, 31 with a retaining element or flange 32, sometimes referred to as a retention disc, at its outer end 33, and a hollow, apertured dome 34 at its inward end 35, all formed of an elastomeric material, such as a silicone rubber. The elastomeric material may be a composition of most any elastomer that is medically acceptable for use in the stoma of a patient and has the ability to promptly recover its natural state or shape after being deformed. Silicone rubber and polyurethane are the preferred elastomers, with silicone rubber being most preferred; rubber latex and styrene-butadiene-rubber latex being less preferred.

Figure 1:
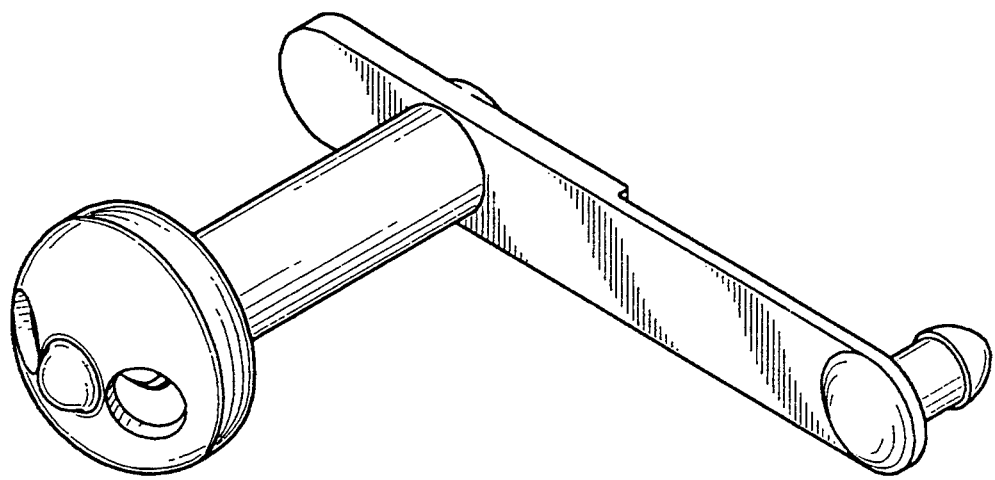
FIG. 1 is an isometric view of a low profile gastrostomy tube according to the prior art showing a hollow shaft with a perforated dome at the inner end of the shaft and with opposed retention wings or flanges at the outer end with a plug for the outer end of the shaft attached to one of the wings by a flexible membrane.
Figure 2:
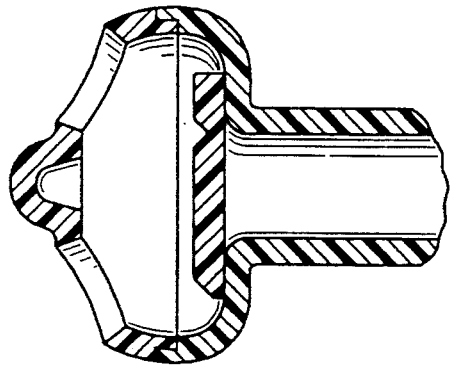
FIG. 2 is a fragmentary view in section of the dome and a portion of the inner end of the shaft of the device of FIG. 1 showing that the wall of the dome is of uniform thickness from apex to bottom wall, and, that there is within the dome a one-way flapper valve adapted to prevent the movement of any fluids out of the stomach into the shaft, and with the valve in the closed position.
Figure 3:
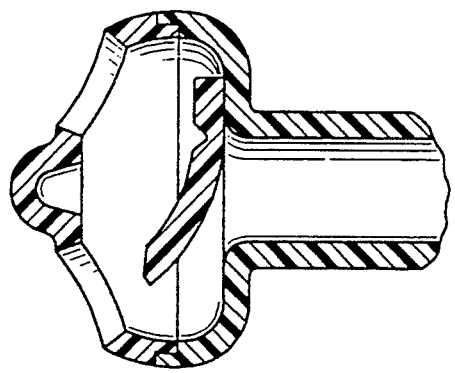
FIG. 3 is a fragmentary view like that of FIG. 2 showing the flapper valve in the open position as it would be when pushed partly open by an obturator or if pushed by a flow of feeding fluid. Such a valve may be defeated or rendered ineffective if sufficient tension is placed on the dome to deform the bottom wall where the flapper valve seats, e.g., by patient weight gain thickening the body wall or by normal movement on the part of the patient.
Figure 4:
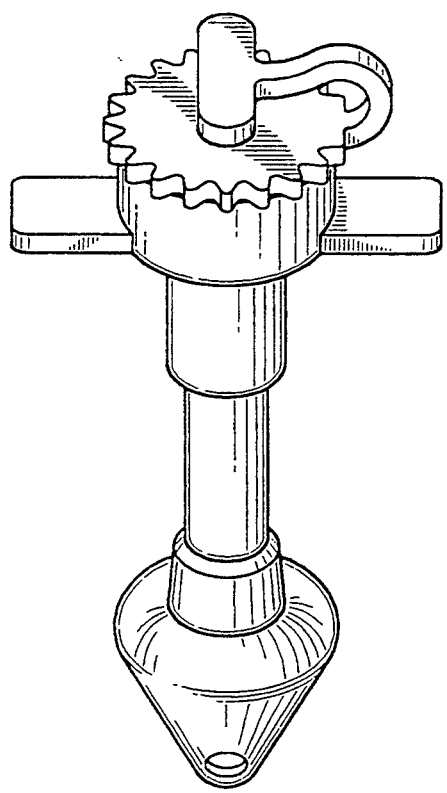
FIG. 4 is an isometric view of another form of gastrostomy transport tube according to the prior art showing a hollow shaft with a conical dome joined at the inner end of the shaft and with a closure of the shaft at the outer end thereof.
Figure 5:
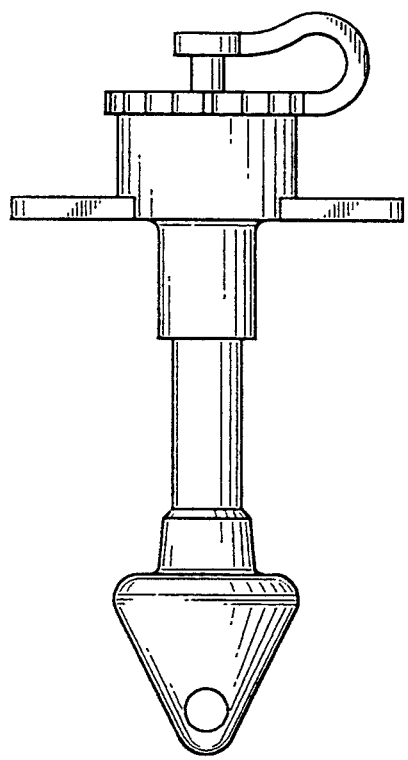
FIG. 5 is a view in side elevation of the device of FIG. 4.
Figure 6:
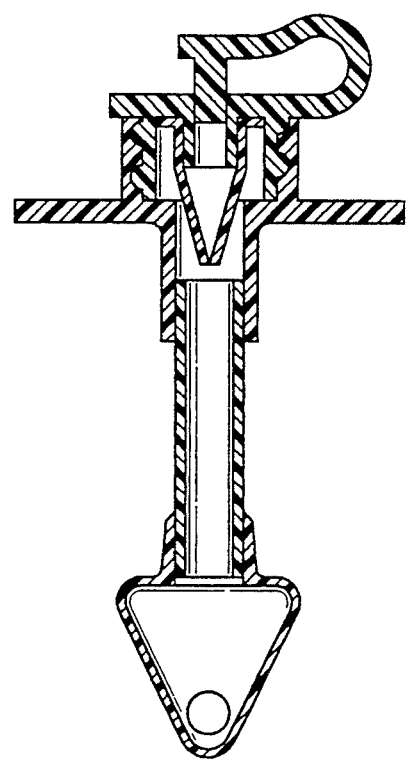
FIG. 6 is a view in longitudinal section of the device of FIGS. 4 and 5 showing that the wall of the dome is of uniform thickness from the apex to the bottom wall, and, that the closure at the outer end of the shaft is a hollow threaded cap fitting within an extension of the retaining element that is attached around the outer end of the shaft, and that there is a duckbill one-way slit valve within the threaded cap.
Figure 7:
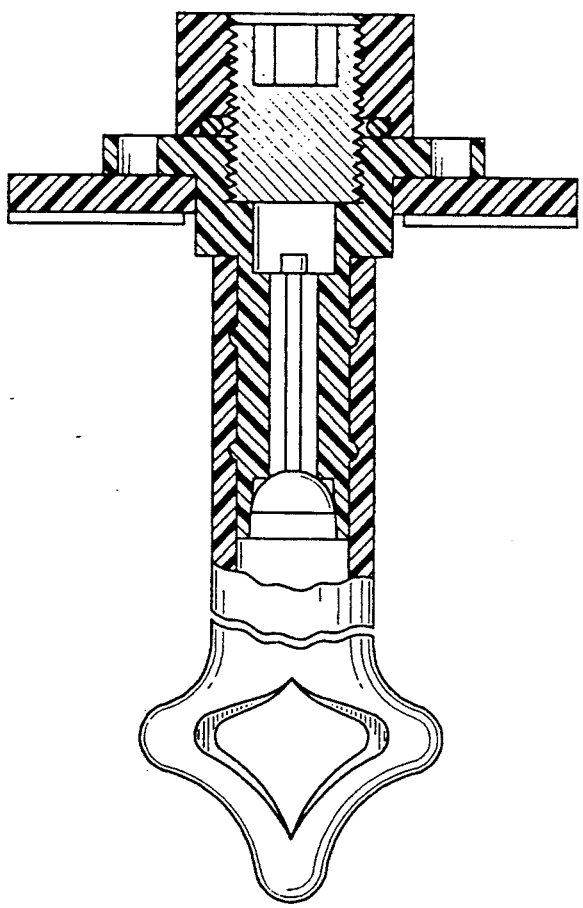
FIG. 7 is view in longitudinal section of yet another prior art gastrostomy device having a somewhat different shaped dome and with a one-way valve within the shaft and adjacent the dome, the one-way valve having a hemispherical valve element attached to a valve guide and seating into a hemispherical valve seat through which the valve stem extends.
Figure 8:
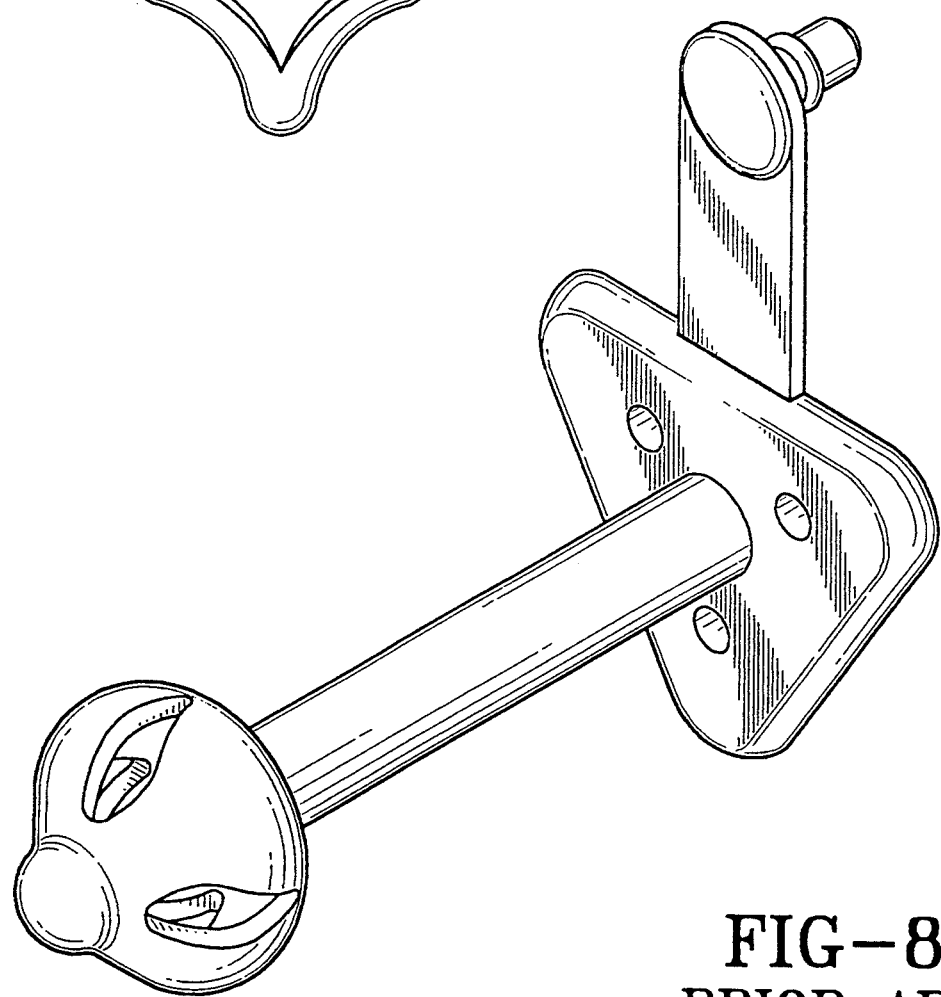
FIG. 8 is an isometric view of yet another prior art low profile gastrostomy device having a hollow shaft with a dome attached at the inner end thereof and a perforated triangular retaining flange at the outer end with an attached plug for closure of the shaft.
Figure 9:
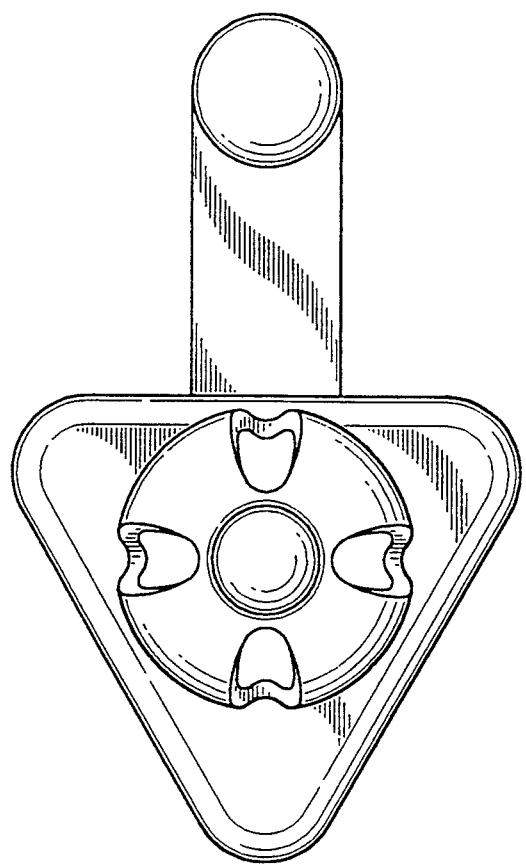
FIG. 9 is a view in end elevation of the device of FIG. 8 showing four apertures or perforations in the wall of the dome and a reinforced apex.
Figure 10:
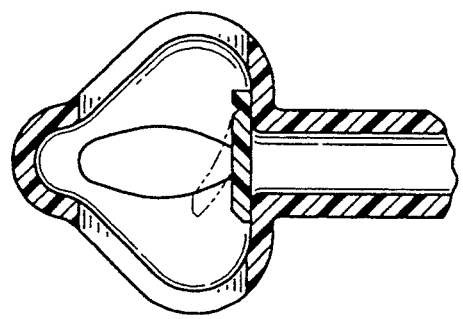
FIG. 10 is a fragmentary view in section of a portion of the inner end of the shaft and the attached dome of the device of FIGS. 8 and 9, showing that the wall of the dome is of uniform thickness from apex to bottom wall and that a flapper valve is used as a one-way valve.
Figure 14:
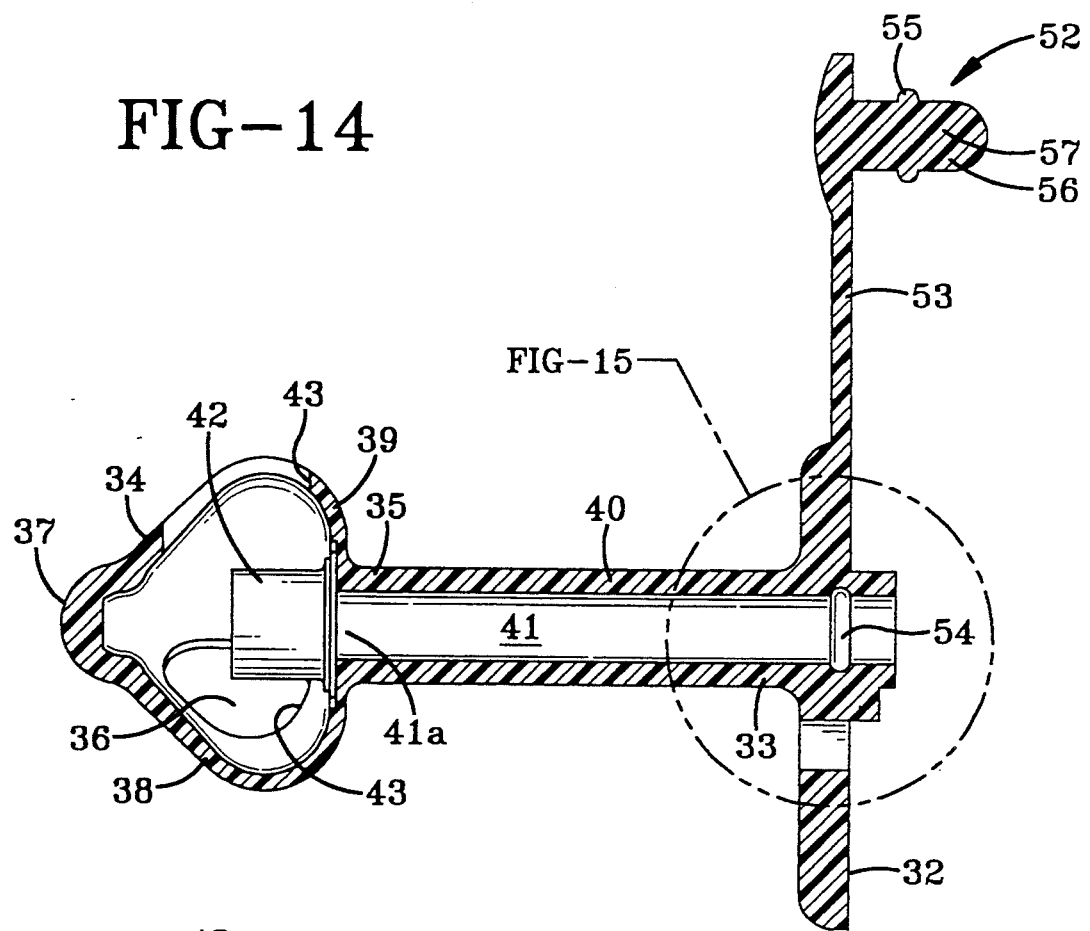
FIG. 14 is a view in longitudinal section of the novel gastrostomy tube of FIG. 11.

Referring now to sectional view FIG. 14 as well as FIG. 1, the dome 34 is seen to have an apex 37, a sidewall 38 that is circular in section, and a bottom wall 39 opposite the apex, the bottom wall 39 being substantially planar except for the interruption of the communicating shaft 31 and the bottom wall 39 being integrally formed with the sidewall 40 of the shaft 31 and substantially planar, although the bottom wall may be adhesively bonded to the shaft portion, if desired. The passageway 41 of the shaft 31 communicates with the interior of the dome 34, via a one-way valve 42, the cylindrical body of which extends into the dome portion 34 from about the bottom wall 39 of the dome portion where the valve is mounted on the inner end 35 of the tubular shaft portion 31.

The shaft 31 will ordinarily have a length of from about 1.5 centimeters to about 4.3 centimeters, depending upon the patient in which the device is to be used. The shaft diameter will be in the range of about 18 to about 28 French, i.e., 0.236 to 0.367 inch (6 to 9.3 millimeters).

As seen in FIG. 14, the sidewall 38 of the dome 34 decreases in thickness from about two-thirds the height of the dome to the bottom wall 39. It is a critical aspect of this invention that the sidewall 38 is sufficiently thinned progressively as the diameter of the dome 34 increases from about mid-height, and preferably from about two-thirds height, of the dome to bottom wall 39 so that the dome, when elongated by the use of an obturator, elongates by stretching smoothly and evenly with substantially no wrinkling or puckering and readily narrows down substantially to the diameter of the tubular shaft. For silicone rubber devices with an upper dome wall thickness in the range of about 0.075 inch (1.68 millimeters) to about 0.060 inch (1.52 millimeters) the wall will be thinned to about 0.040 to 0.030 inch (1.02 to 0.76 millimeters), the extent of wall thinning being preferably at least 20% and not more than about 50% and most preferably about 30 to 35%. The bottom wall of the dome should have a thickness very close to that of the adjacent dome sidewall.

For devices made of different elastomers those skilled will readily perceive how to adjust wall thickness, taking into account the properties of the material, the stronger materials with greater tensile strength dictating a somewhat thinner sidewall than that illustrated for silicone rubber.

For example, for a 22 French size device, the wall thickness will vary from about 0.060 in. (1.5 mm.) near the apex to about 0.040 in. (1 mm.) near the bottom wall for a dome about 0.72 in. (18.3 mm.) in height. Typically, the dome 34 will be about 0.7 to about 0.85 in. (17.8 to about 21.6 mm.) in both height and width depending on whether the device is intended for use by an adult or a child. The dome employed is often a bit taller than it is wide. The dome is preferably substantially conical in shape.

As seen in FIGS. 11, 12 and 14, the dome 34 is provided with three oval apertures 36 for the egress of fluids fed through the shaft 31, although a plurality of two to four or more apertures may be used, if desired. The apertures 36 are substantially equally spaced about the perimeter of the dome 34. These apertures 36 each have their major axis lying approximately along a shortest line extending from the apex 37 to the bottom wall 39, with the lowest edge 43 of each aperture 36 adjacent the bottom wall 39 to aid in good fluid movement out of the dome, which is an advantage in that little residue of nutrient and other solutions administered are to be found in the dome after ordinary rinsing.

The size of the apertures 36 is not sharply critical. The apertures should be large enough to permit ready dissemination of fluids injected through the shaft 31, but not so large as to prevent the dome 34 from performing its retention function, i.e., if there is insufficient sidewall between apertures the sidewall will be overly flexible. Preferably, the apertures are oval with the major axis longitudinal of the dome, the major axis having a length in the range of about 0.3 to about 0.6 inch (7.5 to 15 millimeters) and the minor axis a length in the range of about 0.2 to about 0.4 inch (5 to 10 millimeters) for a dome about 0.65 to 0.8 inch (16.5 to 20.3 millimeters) in height and width. Preferably, the length of the major axis will be in the range of about 0.3 to about 0.5 inch (7.6 to 12.7 millimeters) and the length of the minor axis in the range of about 0.2 to about 0.3 inch (5 to 7.6 millimeters) for a dome in this size range with three apertures.

Figure 14A:
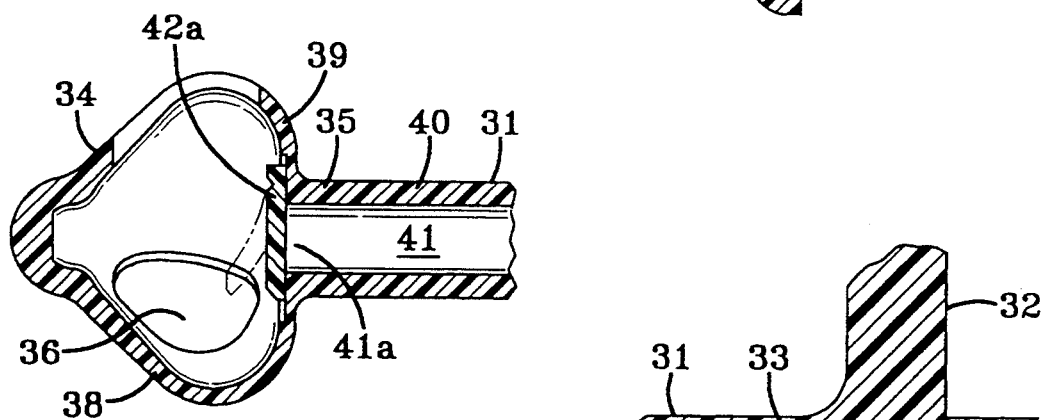
FIG. 14A is a fragmentary portion of a view similar to FIG. 14 showing mainly the dome portion of the device and illustrating the combination of the improved dome of the invention with a conventional flapper valve positioned therein at the inner end of the shaft.

The one-way valve 42 is preferably a slit valve of novel design as seen in FIGS. 14 and 16-19, but may also be a flapper valve 42a of conventional design as shown in FIG. 14A. The flapper valve 42a is hingedly attached simply to the interior face of the bottom wall 39 of the dome 34 at the end 35 of shaft 31 so as to lie or seat across the passageway opening 41a and some of the adjacent interior face of the bottom wall 39 of the dome 34 and provide one-way valve action to prevent reflux of intragastric fluids out of the gastrostomy tube while permitting ready passage of fluids such as nutrients into the stomach of the patient, or, allowing the passage of an obturator during insertion of the device.

Preferably, the valve employed is the novel valve 42, shown and described and claimed in our copending application, Ser. No. 08/069,035, filed May 28, 1993. This valve is here seen in FIGS. 16-19 to consist of a foreshortened hollow cylindrical body portion 44 having first and second ends and an axis, and within which two substantially identical and mutually intersecting partially folded wall portions, indicated generally by the reference numerals 45 and 45a, each V-shaped in section, the folds forming the ridges or apices, are each disposed at a right angle to the other to form a ridge and valley structure in which each wall merges and joins with the other at each valley, there being four quadrants and four valleys within the hollow cylindrical body portion 44 extending entirely across the passageway of the cylindrical body. The folded wall portions 45,45a each extend substantially diametrically of the cylindrical body with the V's both opening in the same axial direction of the cylindrical body 44, toward the first end, and with the lines or lands 46,46a each formed by a respective apex of one of the folded wall portions 45,45a extending along a plane diametrical and substantially normal to the wall of the cylindrical body 44 and each meeting and joining the other land at an angle of about 90 degrees at the center of curvature of the cylindrical body 44 to form four quadrants 47 within the cylindrical body 44. Each wall portion 45,45a ends laterally midway around a quadrant where the wall portion meets, merges and is integrally joined to the other mutually intersecting wall portion to form a valley 48, four valleys in total, that each extend radially outwardly as well as away at an angle, generally, of about 50 to about 65 degrees from the plane in which the apices meet to form the lands 46,46a, extending in the upstream direction of the shaft 31, that is, in the direction the valve will not permit fluids to move, which is also in the direction of the flange structure 49 at the first end of the cylindrical body 44. The flange structure 49 facilitates adhesive bonding or otherwise attaching the cylindrical valve body 44 to the inward end 35 of shaft 31 with the valve within the hollow dome 34.

The surface of each land 46,46a is preferably flat and in said plane and each land is slit entirely through the wall thereof at the intersection thereof with the other land using a sharp instrument to produce very fine intersecting slits 50,50a, each extending along a line about midway of the width of the land surface and about 60 to 80 percent, and preferably about 65 to 75 precent, of the radial length of the land from the intersection 51 of the slits 50,50a to the wall of the cylindrical body 44. The slit lengths are ordinarily in the range of about 1.5 to about 2.5 millimeters.

While the presence of the circumferential cylindrical body wall and its hoop strength is highly essential to the non-leaking or very low leakage behavior of the novel cross-slit one-way valve, the width and thickness of the lands is also critical to the one-way valve operation if significant leakage is to be avoided. If the lands are too narrow, or too thin, there is not sufficient integrity, and serious leakage is likely to occur, while the size requirements of gastrostomy tubes limits the thickness of the folded walls that may be used forming the lands. The width of each land should be, broadly, in the range of about 0.005 to 0.025 inch (0.13 to 0.635 millimeters). Preferably the width of the lands should be in the range of about 0.008 to 0.02 inch (0.20 to 0.50 millimeters), more preferably about 0.01 to about 0.018 inch (0.25 to 0.46 millimeters). The thickness of the lands should be about 0.005 to about 0.030 inch (0.127 to 0.762 millimeters), preferably about 0.010 to about 0.025 inch (0.25 to 0.635 millimeters), and more preferably about 0.015 to about 0.025 inch (0.336 to 0.635 millimeters). These dimensions are given for the device made of silicone rubber. For other elastomeric materials of greater strength properties the dimensions may be slightly smaller, and vice versa if lower strength materials are used.

Figure 18:
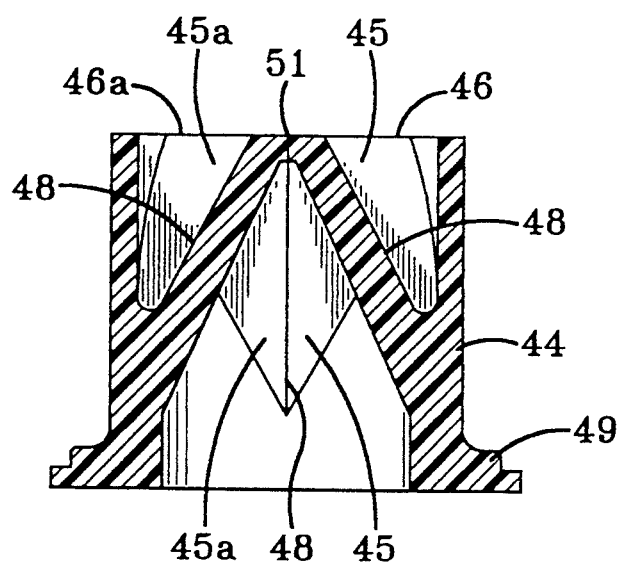
FIG. 18 is a view in section of the valve of FIG. 17 taken in the axial direction along the line 18—18.

Referring now to the sectional view in FIG. 18 there is shown to the left side the integrally formed valley 48 in section at a junction between the respective folded walls 45,45a, then to the rear and in full, the next valley 48, and to the right side the next valley 48 in section, the folded wall portions 45,45a each being integrally formed with the wall of the cylindrical body portion 44.

Figure 16:
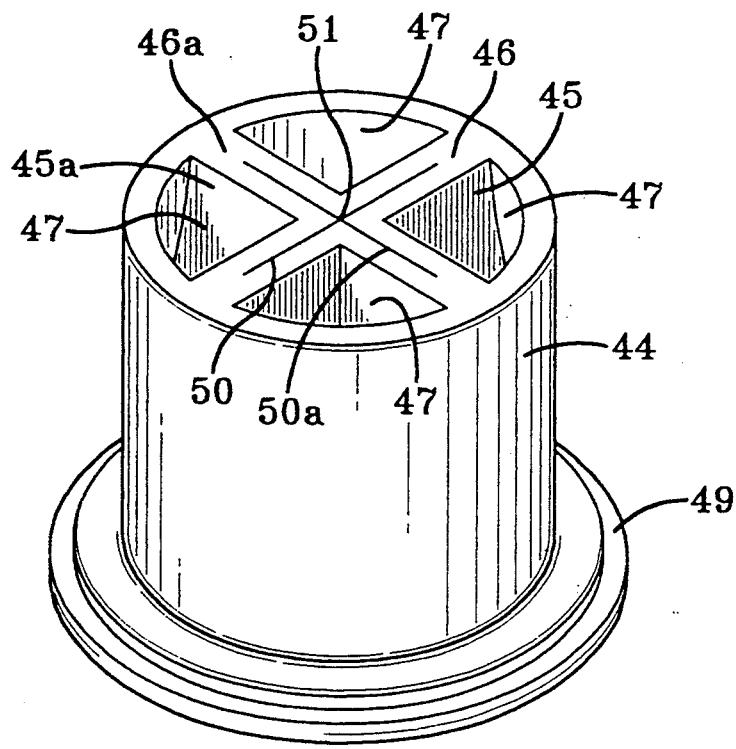
FIG. 16 is an isometric view of the novel cross slit valve utilized in the preferred embodiment of the present gastrostomy tube, the novel valve being seen as a part of the device shown in FIGS. 11 and 14.
Figure 17:
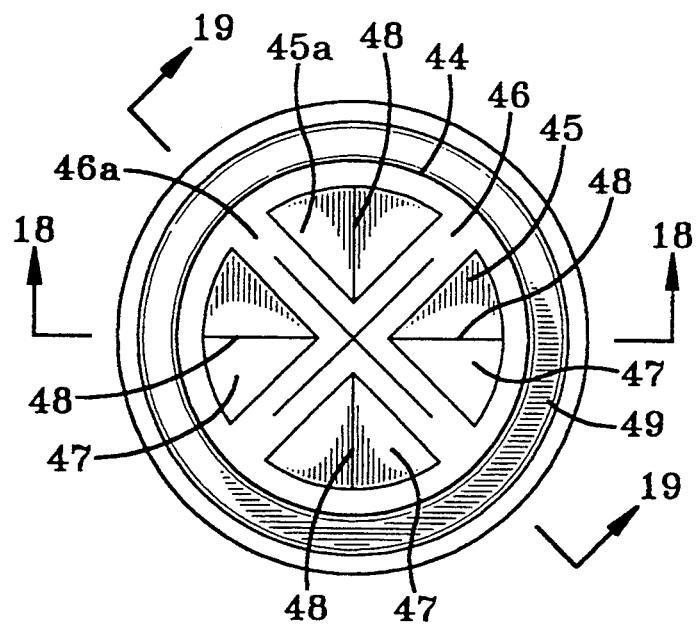
FIG. 17 is a plan view of the valve shown in FIG. 16.
Figure 19:
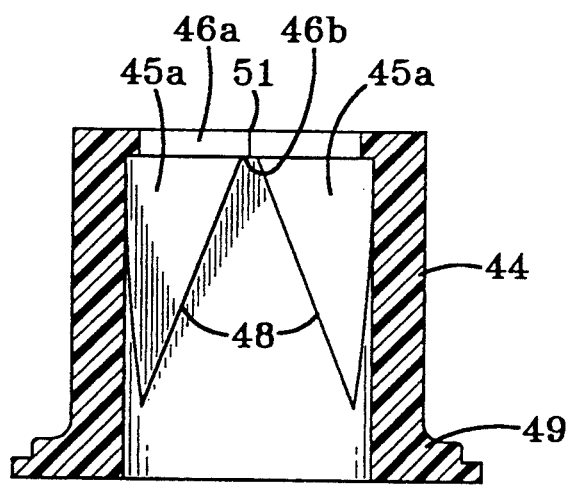
FIG. 19 is a view in section of the valve of FIG. 17 taken in the axial direction along the line 19—19 that lies along a different diameter than followed in FIG. 18, in this case sectioning the land of one of the apices right along the slit therein so that the land does not appear in section except at the unslit portions near the cylindrical body wall.
Figure 20:
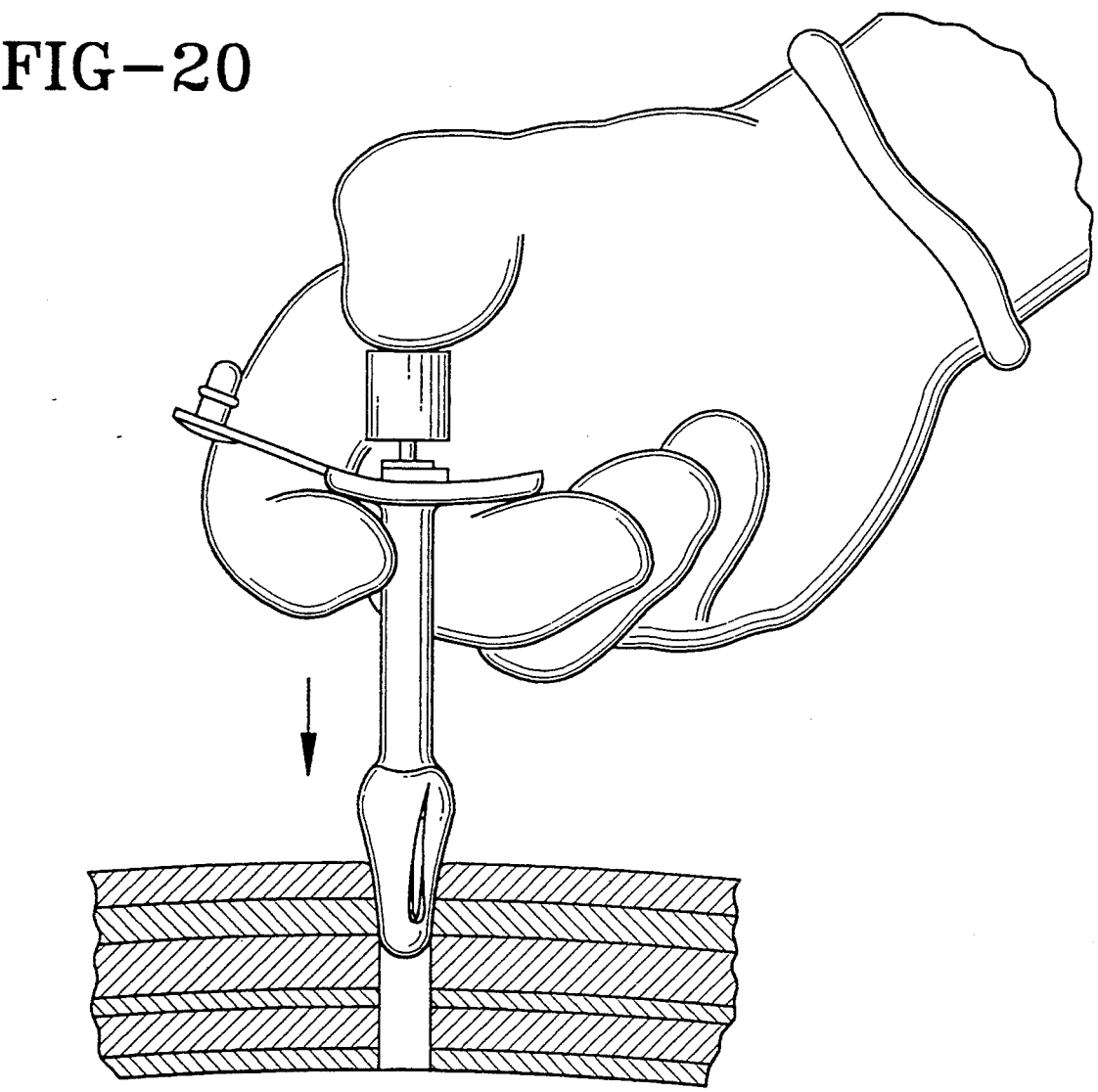
FIG. 20 is a view demostrating the insertion of the novel gastrostomy tube, shown in full, into an established stoma, shown in section, in the abdominal wall and stomach of a patient using an obturator and illustrating the smooth, even walled elongation of the dome of novel design.
Figure 21:
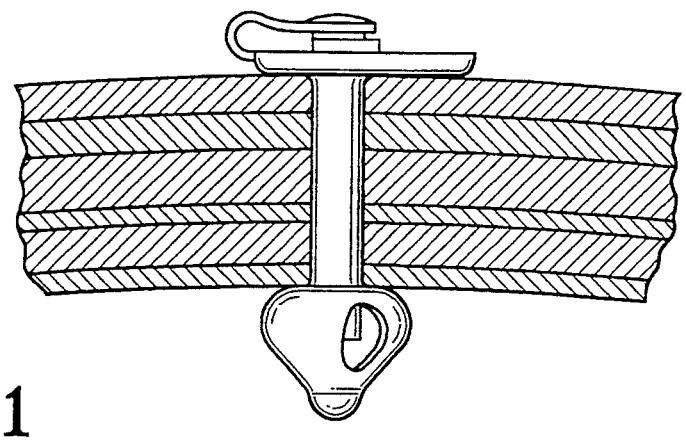
FIG. 21 is a view showing the novel gastrostomy tube of FIG. 20 in place after insertion in the stoma of a patient and with the plug inserted in the shaft adjacent the retaining element.

Referring next to the sectional view in FIG. 19 there is seen land 46a integrally formed with the wall of the cylindrical body portion 44 and sliced along the line of the sectional view exposing the thickness of the land, the slit 50a, seen also in FIG. 16, not extending the full diametric length of the land 46a. The other land 46 that extends at right angles to the visible land 46a extends out of view back from the intersection 51 of the intersecting slit 50 at mid-width of the visible land 46a. Each valley line 48 demarcates the junction of the folded wall 45a, of which the slitted land 46a is visible in this view, with the companion intersecting folded wall 45 that is hidden in this view. The underside of the nearly hidden land 46 is aligned with the short line at 46b that appears in this view just below the intersecting slit 50 at intersection 51 and between the angularly extending folded wall portions 45a.

This construction of the operative valve portion of the cross-slit duckbill valve gives a very positive one-way valve action, greatly inhibiting the possiblities of reflux of intragastric fluids, while still facilitating the use of an obturator in elongating the dome of the device during insertion through a stoma as well as to accomplish decompression. Additionally, this valve construction permits ready introduction of fluids such as nutrient solutions or slurries. The flange structure 49 also permits 360 degree adhesive attachment of the valve body 42 to the inward end 35 of shaft 31 with resulting significant reduction in the possibility of dislodging the novel cross-slit valve from the end of the shaft as compared to dislodging a conventional, simpler flapper valve which can be attached at one side only.

Figure 15:
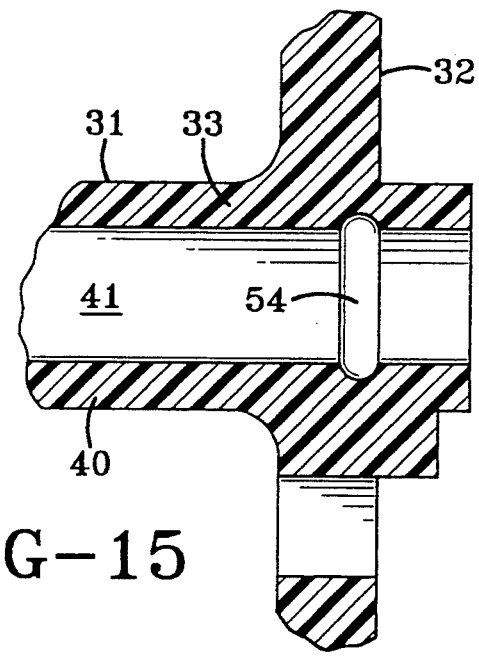
FIG. 15 is an enlarged fragmentary view in section of the portion of of FIG. 14 indicated by the broken line circle.

Referring now to FIGS. 11, 14 and 15, the outward end 33 of the shaft 31 of the gastrostomy tube 30 has integrally formed therewith a retaining portion or flange 32 that bears against the skin of the patient when the device is in use and is preferably flat and more preferably triangular so that it can be rotated occasionally for care of the skin surrounding the site. Preferably the flange 32 is perforated a plurality of times, for example three times, about equally spaced around the outer end 33 of the shaft 31 to permit some air to get to the skin surface.

The end of the shaft 31 is conveniently closed by a plug 52. As shown in FIGS. 11-14, the plug 52 is preferably attached to the flange 49 by a flexible membrane or tab 53 to avoid mislaying it. To assure good retention of the plug and a good seal against leakage, the end portion 33 of the shaft 31 is preferably formed with an annular groove 54 in the passageway 41 to receive a complementary circumferential ridge 55 on the cylindrical portion 56 of the body 57 of the plug 52.

Figure 22:
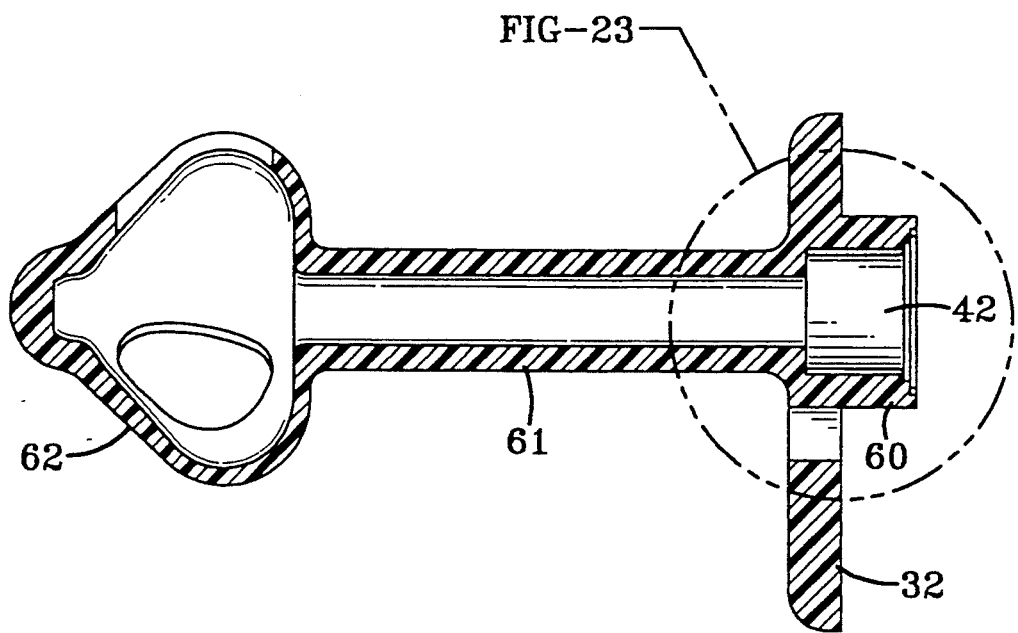
FIG. 22 is a view in section showing the present device similar to that of FIG. 14, but with the cross-slit valve located at the outer end of the tubular shaft in an enlarged section adjacent the retention flange.
Figure 23:
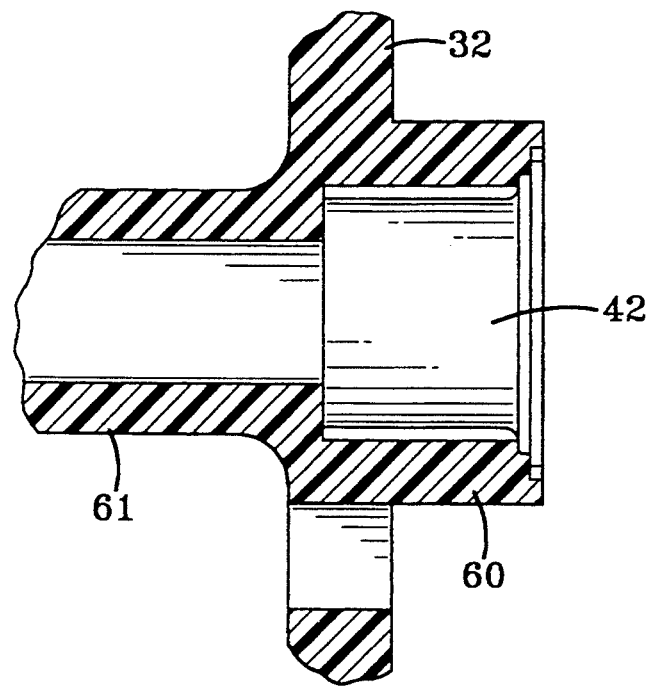
FIG. 23 is an enlarged fragmentary view in section of the portion of FIG. 22 indicated by the broken line circle.
Figure 24:
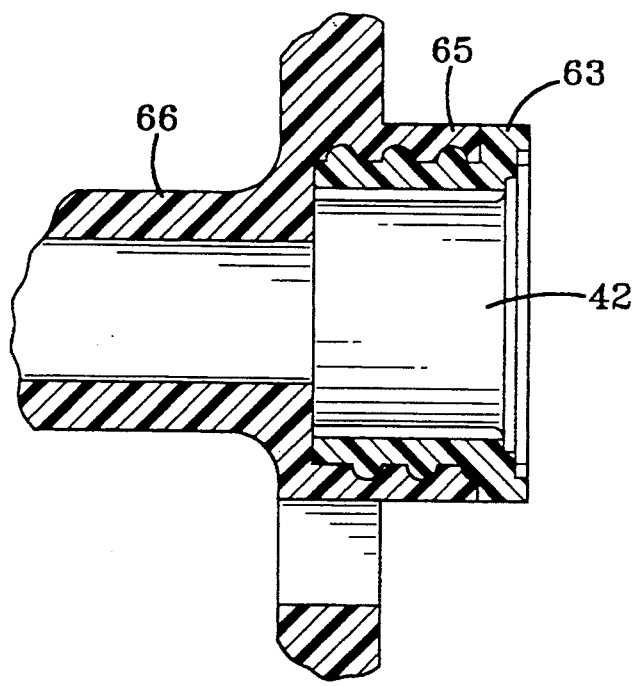
FIG. 24 is an enlarged fragmentary view in section similar to FIG. 23 showing another means of mounting the novel cross-slit valve at the outer end of the tubular shaft, here within an externally threaded sleeve that screws into an internally threaded well that is an extension of the tubular shaft.

As seen in FIGS. 22 and 23, the novel one-way cross-slit valve may be mounted in a device according to the invention as by adhesive bonding at the recessed outward end 60 of a tubular shaft 61 which has attached at the other end a tapered wall dome 62. The fragmentary sectional view in FIG. 24 shows another embodiment in which a removable mount 63 for the novel valve 42 is threadably received in the outer end 65 of a shaft 66 adapted to receive the externally threaded mount, the valve 42 being adhesively bonded by its flange struture to the inside of the threaded mount.

Figure 25:
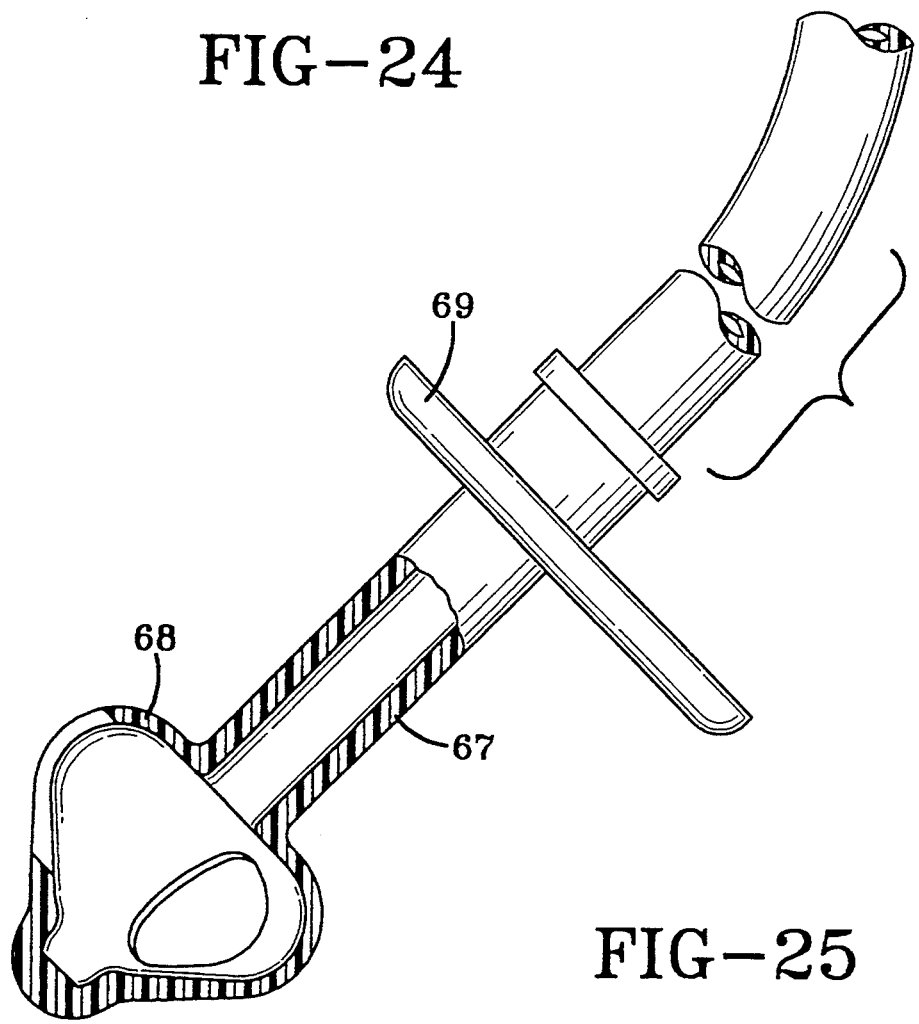
FIG. 25 is a side view, partly in full and partly in section and partly broken to indicate length, showing a gastrostomy tube of the invention with the apertured dome of novel design attached at the inward end of a greatly elongated tubular shaft, the gastrostomy tube having a position-adjustable retention flange but being without a one-way valve.

As seen in FIG. 25, the present device may take the form of a tubular shaft 67, which may be up to a foot long, or longer, having at its inner end a dome 68 of tapered wall according to the invention, and slideably placed thereon, an adjustable retention flange 69, the device in this embodiment not utilizing a one way valve.

We claim:

1. A gastrostomy device formed of elastomeric material and designed to be inserted into an existing stoma of a patient, comprising:
   a. a hollow tubular shaft portion having an inner end and an outer end and a continuous tubular wall defining a longitudinal passage extending completely through the shaft portion, the outer end of the tubular shaft portion being adapted to extend outwardly of the stoma;
   b. an enlarged resiliently deformable hollow dome portion, the dome portion having an apex, a substantially planar bottom wall opposite the apex, and a defining sidewall that has a perimeter and is circular in section and provided with a plurality of oval shaped apertures therethrough about equally spaced about the perimeter, each said oval shaped aperture having a major axis, and each major axis lying about on a shortest line from the apex to the bottom wall of the dome portion and an end of each oval opening being adjacent the bottom wall, the bottom wall being attached to the inner end of the hollow tubular shaft portion, the dome portion having a distal end and an attached end, the distal end being the apex extending away from the tubular shaft portion, and the attached end being the bottom wall, the inner end of the tubular shaft portion extending sealingly through the bottom wall and into the dome portion and communicating with the dome portion, the dome portion being particularly characterized by the defining sidewall thereof being varied in thickness, the thickness of the sidewall gradually decreasing sufficiently from at least about the mid-height of the dome to the bottom wall whereby the dome when elongated with an obturator stretches and elongates smoothly and evenly and readily to substantially the diameter of the hollow tubular shaft; and
   c. a retention flange with a central aperture therethrough and the outer portion of the tubular shaft portion extending slideably therethrough, and the retention flange being adjustably fixable in position upon the tubular shaft portion relative to the dome portion.

2. The gastrostomy device of claim 1 further comprising a one-way valve which is attached to the inner end of the tubular shaft portion within the dome portion so as to substantially prevent passage of fluid from the dome portion into the tubular shaft portion but permit passage of fluid into the dome portion from the tubular shaft portion.

3. The gastrostomy device of claim 2 wherein the dome portion is substantially conical.

4. The gastrostomy device of claim 2 wherein the wall thickness of the dome portion gradually decreases in thickness between at least mid-height of the dome and the bottom wall by at least about 20% and up to about 50%.

5. The gastrostomy device of claim 4 wherein the wall thickness of the dome portion decreases by at least about 30 to 35%.

6. The gastrostomy device of claim 4 wherein the sidewall of the dome portion gradually decreases in thickness starting from about mid-height to about two-thirds the height of the dome and extending about to the bottom wall.

7. The gastrostomy device of claim 2 wherein the defining sidewall of the dome portion varies in thickness from about 0.76 to about 1.68 millimeters from the bottom wall to the region of about the mid-height to the two-thirds height of the dome portion.

8. The device of claim 7 wherein the defining sidewall varies in thickness from about 1.02 to about 1.52 millimeters from the bottom wall to said region.

9. The gastrostomy device of claim 2 wherein the apertures are substantially oval, each with a major axis, and three or four in number, are of substantially equal size and substantially equally spaced about the perimeter of the defining sidewall of the dome portion, the major axis of each opening lying about on a shortest line from the apex to the bottom wall of the dome portion and an end of each oval aperture being adjacent the bottom wall.

10. The gastrostomy device of claim 2 in which the diameter of the bottom wall of the dome portion and the length of the dome portion from bottom wall to apex are each independently a length in the range of about 17.8 to about 21.6 millimeters, and the bottom wall substantially defines a plane and the oval apertures extend to about 1 to 3 millimeters from the plane of the bottom wall.

11. The gastrostomy device of claim 2 wherein the dome has a greater wall thickness at the apex than in the defining wall to withstand greater force from an obturator.

12. The gastrostomy device of claim 2 wherein the one-way valve is a flapper valve.

13. The gastrostomy device of claim 2 wherein the one-way valve is a cross-slit duckbill valve.

14. A low profile gastrostomy device formed of elastomeric material and designed to be inserted into an existing stoma of a patient, comprising:
   a. a hollow tubular shaft portion having an inner end and an outer-end and a continuous tubular wall defining a longitudinal passage extending completely through the shaft portion and the tubular shaft portion is up to about 4.3 centimeters in length and has surrounding the outer end thereof a retention flange adapted to bear against the skin of the abdominal wall of the patient into whose stomach the gastrostomy device is to be inserted;
   b. an enlarged resiliently deformable hollow dome portion, the dome portion having an apex, a substantially planar bottom wall opposite the apex, and a defining sidewall that has a perimeter and is circular in section and provided with a plurality of oval shaped apertures therethrough about equally spaced about the perimeter, each said oval shaped aperture having a major axis, and each major axis lying about on a shortest line from the apex to the bottom wall of the dome portion and an end of each oval opening being adjacent the bottom wall, the bottom wall being attached to the inner end of the hollow tubular shaft portion, the dome portion having a distal end and an attached end, the distal end being the apex extending away from the tubular shaft portion, and the attached end being the bottom wall, the inner end of the tubular shaft portion extending sealingly through the bottom wall and into the dome portion and communicating with the dome portion, the dome portion being particularly characterized by the defining sidewall thereof being varied in thickness, the thickness of the sidewall gradually decreasing sufficiently from at least about the mid-height of the dome to the bottom wall whereby the dome when elongated with an obturator stretches and elongates smoothly and evenly and readily to substantially the diameter of the hollow tubular shaft; and
   c. a one-way cross-slit duck bill valve is attached to the inner end of the tubular shaft portion within the dome portion so as to substantially prevent passage of fluid from the dome portion into the tubular shaft portion but permit passage of fluid into the dome portion from the tubular shaft portion, the cross-slit duck bill valve has a foreshortened hollow cylindrical body within which two folded wall portions together form a ridge and valley structure entirely closing the hollow cylindrical body, each wall portion being V-shaped in section and extending substantially diametrically of the hollow cylindrical body with the V's both opening in the same axial direction of the cylindrical body, and, with the lines formed by the apex of each folded wall portion lying substantially in a common plane substantially normal to the hollow cylindrical body, each wall portion meeting at about right angles to form four quadrants, each wall portion ending midway around a quadrant where it meets and is integrally joined to the mutually intersecting wall portion to form a valley extending radially outwardly from the intersection of the apices as well as at an angle from the said common plane, the so-shaped integral wall being a continuous wall of substantially uniform thickness within the confines of the cylindrical body and integrally formed therewith to make the complete closure, the apices both being slit at the intersection thereby providing intersecting slits, the slits extending entirely through the wall at the fold forming each apex, and the apices facing toward the apex of the dome portion.

15. The gastrostomy device of claim 14 wherein the cross-slit duckbill valve is positioned within the dome portion with the slit apices at about the midlength of the major axes of the oval apertures.

16. The gastrostomy device of claim 14 wherein the intersecting slits are about 1.5 to about 2.5 millimeters in length.

17. The gastrostomy device of claim 14 wherein the apices take the form of flat lands that are about 0.127 to about 0.635 millimeters in width.

18. The gastrostomy device of claim 17 wherein the lands are about 0.20 to about 0.50 millimeters in width.

19. The gastrostomy device of claim 14 wherein the apices take the form of flat lands that are about 0.127 to about 0.762 millimeters thick.

20. The gastrostomy device of claim 19 wherein the lands are about 0.254 to about 0.635 millimeters thick.

21. The gastrostomy device of claim 14 wherein the cylindrical body of the cross-slit duckbill valve has a first and a second end, the first end being a distal end and the second end having a flange structure that is adhesively bonded to the inner end of the tubular shaft portion.

22. The gastrostomy device of claim 14 wherein the retention flange is triangular, is substantially centered about the outer end of the tubular shaft portion and has at least three perforations therethrough.

23. The gastrostomy device of claim 2 wherein removable means is provided for closing the outer end of the hollow tubular portion.

* * * * *